Figure 1:
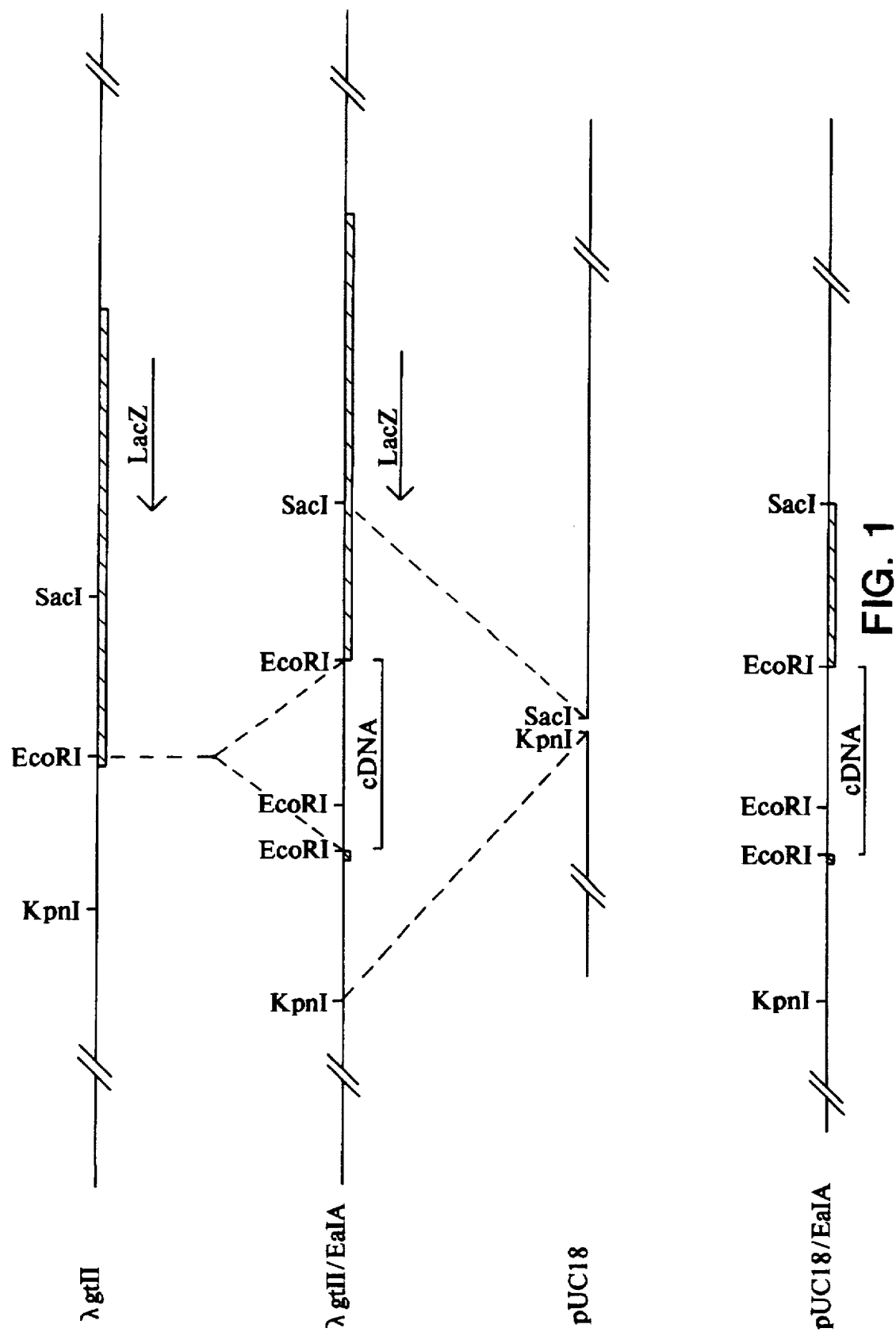

United States Patent [19]

Vermeulen et al.

[11] Patent Number: 5,783,197
[45] Date of Patent: Jul. 21, 1998

[54] EIMERIA POLYPEPTIDE ANTIGEN AND VACCINES CONTAINING THE SAME

[75] Inventors: Arno Vermeulen, Cuyk; Rein Dijkema, Oss; Jacobus Johannes Kok, Nijmegen, all of Netherlands

[73] Assignee: Akzo Nobel N.V., Arnhem, Netherlands

[21] Appl. No.: 473,466

[22] Filed: Jun. 7, 1995

Related U.S. Application Data

[62] Division of Ser. No. 371,947, Jun. 27, 1989, Pat. No. 5,602,033.

[30] Foreign Application Priority Data

Jun. 27, 1988 [NL] Netherlands ............ 88.01627

[51] Int. Cl.⁶ ............ A61K 39/00; A61K 39/012; C12P 21/06
[52] U.S. Cl. ............ 424/267.1; 424/184.1; 424/185.1; 424/271.1; 530/350; 435/69.1; 435/69.3; 435/252.33
[58] Field of Search ............ 424/265.1, 271.1, 424/184.1, 185.1; 435/252.33

[56] References Cited

U.S. PATENT DOCUMENTS

| | | | |
|---|---|---|---|
| 4,639,372 | 1/1987 | Murray et al. | 424/88 |
| 4,710,377 | 12/1987 | Schenkel | 424/88 |
| 4,724,145 | 2/1988 | Murray et al. | 424/88 |
| 4,874,705 | 10/1989 | Andrews et al. | 435/252.33 |
| 5,028,694 | 7/1991 | Mewman et al. | 530/350 |
| 5,279,960 | 1/1994 | Anderson et al. | 435/243 |

FOREIGN PATENT DOCUMENTS

| | | |
|---|---|---|
| 0256536 | 2/1988 | European Pat. Off. |
| WO 86/00528 | 1/1986 | WIPO |

OTHER PUBLICATIONS

Clarke et al Molecular & Biochem. Parasitology 22:79–87, 1987.
Jenkins et al Experimental Parasilology 66:96–107 1988.
Houghten et al Vaccines 86 pp. 521–525, 1986.
M.C. Jenkins et al., Federation Proceedings, 46:3:#2696, 1987.
H. Lillehoj et al., The FASEB Journal, 2:42:A881, #3403, 1988.
M. Jenkins et al., The FASEB Journal, 2:4:A880, #3399, 1988.

Primary Examiner—Hazel F Sidberry
Attorney, Agent, or Firm—Mary E. Gormley; William M. Blackstone

[57] ABSTRACT

The present invention is concerned with a polypeptide of Eimeria which can be used for the immunization of poultry against coccidiosis. Furthermore, the invention comprises a DNA fragment of Eimeria coding for said polypeptide.

4 Claims, 5 Drawing Sheets

| | | | | | | | |
|---|---|---|---|---|---|---|---|
| GLU | PHE | PRO | GLU | GLN | MET | PRO | PRO |

```
G A A T T C C C T G A A C A A A T G C C T C C C
          10                      20
```

| SER | ALA | ALA | ARG | ASP | ASP | LEU | GLU |

```
T C C G C T G C T C G C G A T G A T C T C G A A
          30                      40
```

| ALA | GLY | LEU | LEU | GLU | PHE | GLU | ARG |

```
G C T G G C C T C C T C G A G T T C G A G A G A
50                    60                    70
```

| ASP | GLU | ARG | ALA | ASP | PRO | SER | SER |

```
G A T G A G C G C G C G G A C C C A T C G T C A
          80                      90
```

| TRP | PRO | TYR | PRO | ARG | LEU | ALA | VAL |

```
T G G C C T T A T C C C A G A T T G G C T G T T
      100               110                 120
```

| GLY | VAL | LEU | LYS | ASP | SER | ASN | GLY |

```
G G T G T T C T C A A G G A T T C C A A C G G T
              130                 140
```

| SER | VAL | MET | VAL | PRO | ILE | ALA | PRO |

```
T C A G T C A T G G T G C C C A T T G C C C C G
          150                     160
```

| LYS | PHE | VAL | PRO | ARG | LEU | ARG | LYS |

```
A A G T T T G T T C C A A G G C T C A G A A A G
170                   180                   190
```

| MET | ALA | PHE | ARG | VAL | ILE | VAL | GLU |

```
A T G G C A T T C C G T G T C A T C G T C G A G
              200                 210
```

| SER | GLY | ALA | GLY | ALA | ASN | ALA | GLY |

```
T C C G G T G C T G G C G C G A A T G C T G G C
          220                 230             240
```

| PHE | SER | ASP | GLU | GLU | TYR | ARG | ARG |

```
T T C A G T G A C G A A G A G T A C A G A A G A
              250                 260
```
| ALA | GLY | ALA | GLU | ILE | ALA | SER | ASN |

```
G C T G G A G C A G A G A T T G C G T C C A A C
          270                 280
```

| ALA | ASP | ALA | VAL | ILE | ASN | GLY | ALA |

```
G C C G A T G C A G T C A T C A A C G G A G C T
290                   300                   310
```

| GLU | VAL | LEU | LEU | ARG | VAL | SER | ALA |

```
G A G G T G C T G C T C C G C G T G T C A G C C
              320                 330
```

FIG. 2A

```
PRO  THR  PRO  GLU  MET  VAL  SER  ARG
C C A A C A C C G G A A A T G G T C T C C C G C
   340              350              360

MET  PRO  ARG  ASP  LYS  VAL  LEU  ILE
A T G C C C A G A G A C A A G G T G C T G A T C
                  370              380

SER  TYR  LEU  PHE  PRO  SER  VAL  ASN
A G C T A C C T C T T C C C C A G C G T C A A C
   390              400

THR  GLN  ALA  LEU  ASP  MET  LEU  ALA
A C G C A A G C A T T A G A C A T G C T T G C A
410              420              430

ARG  GLN  GLY  VAL  THR  ALA  LEU  ALA
C G T C A A G G A G T C A C A G C C C T T G C T
            440              450

VAL  ASP  GLU  VAL  PRO  ARG  VAL  THR
G T G G A C G A A G T G C C A C G T G T C A C C
   460              470              480

ARG  ALA  GLN  LYS  LEU  ASP  VAL  LYS
A G A G C A C A A A A G C T A G A C G T T A A G
                  490              500

SER  ALA  MET  GLN  GLY  LEU  GLN  GLY
T C T G C G A T G C A A G G C C T C C A G G G C
            510              520

TYR  ARG  ALA  VAL  ILE  GLU  ALA  PHE
T A T C G C G C A G T C A T T G A A G C A T T C
530              540              550

ASN  ALA  LEU  PRO  LYS  LEU  SER  LYS
A A C G C A C T C C C A A A G C T C A G C A A G
            560              570

ALA  SER  ILE  SER  ALA  ALA  GLY  ARG
G C G T C C A T C A G C G C T G C T G G C C G T
   580              590              600

VAL  GLU  ALA  ALA  LYS  VAL  PHE  VAL
G T T G A G G C T G C C A A G G T T T T C G T T
            610              620

ILE  GLY  ALA  GLY  VAL  ALA  GLY  LEU
A T C G G T G C C G G T G T T G C C G G T C T C
            630              640

GLN  ALA  ILE  SER  THR  ALA  HIS  GLY
C A G G C T A T T T C A A C T G C C C A T G G T
650              660              670
```

FIG. 2B

| LEU | GLY | ALA | GLN | VAL | PHE | GLY | HIS |
|---|---|---|---|---|---|---|---|
T T G G G T G C A C A A G T T T T C G G T C A T
          680                    690

| ASP | VAL | ARG | SER | ALA | THR | ARG | GLU |
|---|---|---|---|---|---|---|---|
G A T G T G C G C T C C G C A A C A C G C A G
    700              710                720

| GLU | VAL | GLU | SER | CYS | GLY | GLY | LYS |
|---|---|---|---|---|---|---|---|
G A G G T C G A A T C T T G T G G T G G A A A G
              730                  740

| PHE | ILE | GLY | LEU | ARG | MET | GLY | GLU |
|---|---|---|---|---|---|---|---|
T T C A T T G G C T T G A G A A T G G G G A G
        750                  760

| GLU | ALA | GLU | VAL | LEU | GLY | GLY | TYR |
|---|---|---|---|---|---|---|---|
G A A G C T G A A G T T C T C G G A G G C T A T
770                  780                    790

| ALA | ARG | GLU | MET | GLY | ASP | ALA | TYR |
|---|---|---|---|---|---|---|---|
G C A C G C G A A A T G G G T G A T G C G T A C
              800                  810

| GLN | ARG | ALA | GLN | ARG | GLU | LEU | ILE |
|---|---|---|---|---|---|---|---|
C A G A G G G C C C A A A G A G A G T T G A T T
          820                  830                  840

| ALA | ASN | THR | ILE | LYS | HIS | CYS | ASP |
|---|---|---|---|---|---|---|---|
G C A A A C A C A A T C A A G C A C T G T G A C
                  850                      860

| VAL | VAL | ILE | CYS | THR | ALA | ALA | ILE |
|---|---|---|---|---|---|---|---|
G T T G T C A T A T G T A C C G C T G C C A T C
              870                  880

| HIS | GLY | LYS | PRO | SER | PRO | LYS | LEU |
|---|---|---|---|---|---|---|---|
C A C G G A A A G C C T T C T C C G A A G C T T
890                      900                      910

| ILE | SER | ARG | ASP | MET | LEU | ARG | SER |
|---|---|---|---|---|---|---|---|
A T C T C A C G C G A C A T G C T G C G C T C A
                  920                  930

| MET | LYS | PRO | GLY | SER | VAL | ILE | VAL |
|---|---|---|---|---|---|---|---|
A T G A A G C C T G G C T C T G T C A T T G T G
          940                  950                  960

| ASP | ILE | ALA | THR | GLU | PHE | GLY | ASP |
|---|---|---|---|---|---|---|---|
G A C A T T G C A A C T G A A T T C G G C G A T
              970                      980

| THR | ARG | SER | GLY | TRP | GLY | GLY | ASN |
|---|---|---|---|---|---|---|---|
A C G C G C T C T G G A T G G G G A G G A A A T
              990                1000

FIG. 2C

```
    VAL   GLU   VAL   SER   PRO   LYS   ASP   ASP
    G T T G A G G T T T C C C C A A G G A C G A C
    1010              1020              1030

GLN   VAL   VAL   VAL   ASP   GLY   ILE   THR
    C A G G T C G T G G T C G A C G G C A T C A C T
              1040              1050

VAL   ILE   GLY   ARG   LYS   ARG   ILE   GLU
    G T C A T T G G A C G C A A A C G C A T T G A A
    1060              1070              1080

THR   ARG   MET   PRO   VAL   GLN   ALA   SER
    A C C C G C A T G C C A G T C C A G G C T T C A
                  1090              1100

GLU   LEU   PHE   SER   MET   ASN   ILE   CYS
    G A G C T G T T C T C C A T G A A C A T C T G C
              1110              1120

ASN   LEU   LEU   GLU   ASP   LEU   GLY   GLY
    A A C C T T C T C G A A G A T C T A G G T G G C
    1130              1140              1150

GLY   SER   ASN   PHE   ARG   VAL   ASN   MET
    G G C A G C A A C T T C C G C G T C A A C A T G
              1160              1170

ASP   ASP   GLU   VAL   ILE   ARG   GLY   LEU
    G A C G A C G A A G T T A T C A G A G G A T T G
              1180              1190              1200

VAL   ALA   VAL   TYR   GLN   GLY   ARG   ASN
    G T T G C C G T C T A T C A A G G C C G C A A C
                  1210              1220

VAL   TRP   GLN   PRO   PRO   GLN   PRO   THR
    G T G T G G C A G C C C C C C A G C C A A C G
              1230              1240

PRO   VAL   SER   ARG   THR   GLU   PHE
    C C C G T C T C A A G A A C G G A A T T C
    1250              1260
```

FIG. 2D

EIMERIA POLYPEPTIDE ANTIGEN AND VACCINES CONTAINING THE SAME

This is a division of application Ser. No. 07/371,947 filed Jun. 27, 1989 now U.S. Pat. No. 5,602,033.

The invention relates to a DNA fragment and an Eimeria polypeptide coded by this, recombinant DNA which contains the particular DNA fragment, host cells with this recombinant DNA and vaccines against coccidiosis which are based on these products.

Coccidiosis is a disease which is caused by intracellular parasites, protozoa, of the subphylum Apicomplexa and the genus Eimeria. These parasites multiply in cells which form part of the gastrointestinal tract and digestive organs of their hosts.

Due to the increasing intensive production, the damage which is caused by these parasites in the poultry industry has risen alarmingly in recent decades. The losses which poultry farmers in the Netherlands suffer every year run into millions of guilders; the loss in 1986 was about 13 million guilders. In the same year a loss of U.S. $ 300 million was suffered in the U.S., despite the use of coccidiostats.

The pathogens of coccidiosis in chickens can be subdivided into nine different types, i.e. Eimeria acervulina, E. maxima, E. tenella, E. necatrix, E. brunetti, E. mitis, E. praecox, E. mivati and E. hagani. However, some people doubt the existence of the last two types. All of these types have only the chicken as host and display a high degree of tissue specificity. The life cycles of the said types are, however, similar.

The types do differ in their pathogenic effect on chickens, the type of chicken also playing a role; thus, a spring chicken will be subjected to a great deal of damage by a parasite such as E. acervulina or E. maxima because these parasitise large portions of the small intestine, where food digestion plays a major role.

During the life cycle, the Eimeria parasites pass through a number of stages. The infectious stage (the sporulating oocyst) is taken in orally and passes into the stomach of the chicken, where the shell of the cyst bursts open as a result of the grinding action. The four sporocysts, which this oocyst contains, are released and pass into the duodenum, whereby they are exposed to bile and digestive enzymes. As a result, an opening is made in the sporocyst wall and the sporozoites present in the sporocyst are released. These sporozoites are mobile and search for suitable host cells, for example epithelium cells, in order to penetrate and to reproduce. Depending on the type, this first reproduction phase lasts 20 to 48 hours and several tens to hundreds of merozoites are formed, which each again penetrate a new host cell and reproduce. After two to sometimes five of these asexual reproduction cycles, the intracellular merozoites grow into sexual forms, the male and female gametocytes. After fertilization of the female by a male gamete, a zygote is formed which creates a cyst wall around itself. This oocyst leaves the host cell and is driven out with the faeces. If the temperature and humidity outside the chicken are relatively high and, at the same time, there is sufficient oxygen in the air, the oocyst can sporulate to the infectious stage.

Thus, no intermediate host is needed for transfer of the parasite from chicken to chicken. It is therefore conceivable that with a high degree of occupation of the available surface area the infection pressure in a chicken farm rapidly increases.

The parasite can be combatted in various ways.

In addition to using good management, coccidiosis can be combatted by using combatting agents which frequently are mixed in the feed or drinking water. However, these agents have suffered a drop in effectiveness in recent years, partly because of the high genetic capacity of the parasite to develop a resistance towards various combatting agents. In addition, a number of these agents leave residues in the meat which can give rise to problems on consumption.

Immunological prophylaxis would, therefore, constitute a much better combatting method. It is known that chickens which have lived through a sufficiently high infection are able to resist a subsequent contact with the same type of Eimeria. Resistance towards Eimeria can also be induced by infecting the birds several times with low doses of oocysts or with oocysts of weakened (non-pathogenic) strains. However, controlled administration to, specifically, large numbers of chickens for slaughter is a virtually insurmountable problem in this case. Inactivated vaccines therefore appear to be the only remaining solution.

An inactivated vaccine can consist of an antigen originating from the parasite, possibly with an adjuvant.

As an alternative for an antigen isolated from parasites, it is possible to use a product prepared with the aid of recombinant DNA technology, a technique which can be carried out according to known methods.

Moreover, vaccination can be carried out by administering a live host organism such as a bacterium, a fungus or a virus in which a gene coding the antigen has been incorporated. This organism then ensures adequate long-term synthesis of antigen so that the immune system of the chicken is adequately stimulated.

At the same time it is possible synthetically to reproduce the antigen or parts thereof and to administer this to the birds in an immunologically recognizable and stimulating form, for example bonded to a carrier protein in the presence of an adjuvant.

According to the present invention it is possible to use a polypeptide or an immunogenic equivalent or part thereof, which is coded by a deoxypolynucleotide which is derived from E. acervulina and is present as an insertion in the plasmid pEa1A, with which the Escherichia coli strain K12JA221 has been transformed, which has been deposited with the Centraal Bureau voor Schimmelcultures, Baarn (The Netherlands) under deposit number CBS 143.88, for the immunization of poultry against coccidiosis.

Furthermore, the present invention comprises also the use of a polypeptide of an Eimeria specie or an immunogenic equivalent or part thereof, which is coded by a deoxypolynucleotide derived of an Eimeria specie and which hybridizes with the inserted deoxypolynucleotide sequence, for the immunization of poultry against coccidiosis.

The abovementioned plasmid pEa1A is prepared by the method given in the experimental section, which is explained here schematically with the aid of FIG. 1.

The phage λgt11 (ref. 4) was treated with the restriction enzyme EcoRI, for which it possesses a single restriction site. A cDNA, prepared on the basis of E. acervulina mRNA, is inserted in this restriction site: λgt11Ea1A. After treatment with the restriction enzymes KpnI and SacI, a phage fragment is isolated from the recombinant phage thus obtained, which fragment consists of the said cDNA and flanking DNA sections originating from the locality of the EcoRI restriction site, in the LacZ gene, of λgt11. The plasmid pUC18 (ref. 6) was likewise treated with KpnI and SacI and then ligated with the previously mentioned phage fragment containing cDNA:pUC18/Ea1A.

The nucleotide sequence which is determined for the cDNA section of this insertion is given in FIG. 2. Likewise the amino acid sequence derived herefrom.

It is known that for a given amino acid frequently several different codons (triplets of nucleotide bases) can code in the DNA. Thus, the codon for GLU (glutamic acid) is for example GAT or GAA, etc. It is obvious that for the expression of the polypeptide with the amino acid sequence according to FIG. 2 (or a fragment thereof) use can likewise be made of a DNA with a similar alternative codon composition.

For expression of the polypeptide according to the invention, use can also be made of a DNA fragment which is obtained by isolating a DNA fragment from the genomic DNA or the cDNA of Eimeria species which, according to known techniques under stringent conditions, hybridizes with the cDNA section of the plasmid Ea1A. If desired, a DNA fragment of this type can also possess, in addition to the cDNA section just mentioned, additional flanking DNA pieces which are coding for polypeptides.

DNA fragments of this type obtained by hybridization and also recombinant DNA molecules which contain these fragments likewise form part of the present invention.

Polypeptides which are coded by these DNA fragments and have protective, immunizing properties also form part of the invention.

In addition, fragments of these polypeptides, which can be used for immunization of poultry against coccidiosis, also form part of the invention. Various methods are known for detecting such usable polypeptide fragments (termed epitopes) within a known or unknown amino acid sequence. On the basis of a known amino acid sequence, these epitopes can, for example, be determined experimentally with the aid of the screening techniques described in patent publications Wo 84/03564 and Wo 86/06487.

In addition, a number of regions of the polypeptide, with the stated amino acid sequence, can be designated epitopes on the basis of theoretical considerations and structural agreement with epitopes which are now known. The determination of these regions was based on a combination of the hydrophilicity criteria according to J. P. Hopp and K. R. Woods (ref. 5) and the secondary structure aspects according to P. Y. Chou and G. D. Fasman (ref. 8).

The following regions contain probable epitopes for antibodies:

$Leu_{20}$—$Arg_{37}$
$Gly_{41}$—$Met_5$
$His_{232}$—$CYS_{245}$
$Glu_{325}$—$Gly_{334}$
$Gly_{335}$—$Val_{346}$
$Gly_{355}$—$Glu_{366}$

T-cell epitopes which may be necessary can likewise be derived on theoretical grounds with the aid of Berzofsky's amphiphilicity criterion (ref. 9).

For immunization against coccidiosis infection in accordance with the present invention it is also possible to use, for example, anti-idiotype antibodies or antigen-binding fragments thereof. Such antibodies are directed against the idiotype of antibodies, which, in turn, are directed against the polypeptide according to the invention. The immunogenic equivalents of the polypeptide according to the invention which have been indicated above are understood to mean, inter alia, anti-idiotype antibodies of this type.

The intended immunization can, for example, be effected by administering the present polypeptide, or an immunogenic section or equivalent thereof, as such to the birds, or by administering to the birds to be immunized a microorganism which has been genetically modified by a recombinant DNA and which is able to produce the polypeptide, or an immunogenic section or equivalent thereof, in situ.

For immunization of poultry against coccidiosis in accordance with the present invention, it is possible, on the one hand, to administer the present polypeptides, fragments or immunogenic equivalents as such to the birds or, on the other hand, if desired to administer microorganisms which by genetic manipulation have acquired the ability to produce the present polypeptides etc. "Subunit vaccines" is a frequently used term for the first case and the term "vector vaccines" is usually used for the second case—we will also adopt this nomenclature here.

The subunit vaccines according to the invention in general contain the polypeptides in purified form, optionally in the presence of a pharmaceutically acceptable excipient. The polypeptide can optionally be covalently bonded to a non-related protein, which, for example, can be of advantage in the purification of the fusion product. Examples are β-galactosidase, protein A, prochymosine, blood clotting factor Xa, etc.

The polypeptides for such applications can be prepared with the aid of known methods, such as by isolation from $E.acervulina$ or other Eimeria species, by means of recombinant DNA techniques or by peptide synthesis.

If desired, the polypeptides can also be modified in vivo or in vitro by, for example, glycosylation, amidation, carboxylation or phosphorylation.

In vector vaccines, the polypeptide product according to the invention is made up by a genetically manipulated organism which is itself administered to the individual to be immunized and which maintains itself for some time, or even reproduces, in the body. Diverse organisms can be used as the host for this purpose, such as, for example, bacteria such as *Escherichia coli*, *Bacillus*, or *Salmonella*, or viruses such as cowpox or avian pox virus. With host organisms of this type, the polypeptide can express itself as a surface antigen. In this context fusion of the said polypeptide with OMP proteins or pilus proteins of *Escherichia coli* or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

EXAMPLE 1

Sporulation of *E. acervulina* oocysts

A suspension of $5 \times 10^8$ *E. acervulina* oocysts in 60 ml $10^{-4}$ M sodium dithionite was centrifuged, after which the pellet was washed once with 100 ml sterile water. The cells were resuspended in 500 ml 2% potassium bichromate and then incubated under the influence of strong aeration for 7 hours at 30° C. The oocysts were then collected by centrifuging and washed three times with 200 ml sterile water.

Isolation of RNA

For the isolation of RNA (ref. 1) the cell pellet was taken up into 2.8 ml of buffer containing 10 mM Tris acetate (pH 7.6), 75 mM sodium acetate, 1% SDS, 2 mM EDTA, 0.2 mg/ml proteinase K and 10 mM vanadyl ribonucleoside complexes. The oocysts were destroyed by vortexing for 60 seconds (max) in the presence of 13 g glass beads (φ 0.5 mm). 5 ml of phenol was added to the total extract and the mixture was vortexed for a further 60 seconds. After centrifuging, the supernatant liquor was pipetted off and again extracted with an equal volume of phenol/chloroform/isoamyl alcohol (25:24:1). RNA was precipitated after adding 2.5 volume ethanol and the resulting precipitate was dissolved in 800 µl Tris 10 mM, EDTA 0.1 mM pH 7.6 ($T_{10}E_{0.1}$), after which the product was extracted a further twice with an equal volume of phenol/chloroform/isoamyl alcohol (25:24:1) and twice with chloroform/isoamyl alcohol (24:1) and then precipitated with ethanol. PolyA$^+$-RNA was isolated by means of oligo(dT)-cellulose chromatography (ref. 2). Approximately 100 µg polyA$^+$-RNA was isolated from $5 \times 10^8$ oocysts.

cDNA synthesis

PolyA$^+$-RNA was converted to cDNA by means of the enzyme MMLV reverse transcriptase. For this purpose 25 µg polyA$^+$-RNA was dissolved in 90 µl of water and denatured for 5 minutes at 20° C. by adding mercury methyl hydroxide to 10 mM, after which P-mercaptoethanol was added to 45 mM and the mixture incubated for a further 3 minutes at 20° C. The enzyme reaction was carried out in 190 µl buffer containing 4 µg oligo(dT)$_{15}$, 150 U RNAsin$^{(R)}$, 20 mM Tris (pH 7.6), 30 mM KCl, 4 mM dithiothreitol (DTT), 2 mM $MgCl_2$, 1 mM of each dNTP and 3000 U MMLV reverse transcriptase. The reaction was stopped after 1 hour's incubation at 37° C. by adding 10 µl 0.5M EDTA. After extraction with an equal volume of phenol/chloroform/isoamyl alcohol (25:24:1), the RNA/DNA hybrid was precipitated by adding ammonium acetate to 2M and 2.5 volumes ethanol. The combined action of the enzymes DNA-polymerase I and RNase H (ref. 3) results in the synthesis of the second string. The pellet was dissolved in 960 µl of buffer containing 20 mM Tris (pH 7.6), 5 mM $MgCl_2$, 100 mM $(NH_4)_2SO_4$, 0.6 mM β-AND, 16 U RNase H, 200 U DNA-polymerase I and 20 U DNA-ligase (*E.coli*). The incubation time was 1 hour at 12° C. and then 1 hour at 22° C., after which the reaction was stopped by adding an equal volume of phenol/chloroform/isoamyl alcohol (25:24:1) and precipitating with ethanol.

Before the cDNA was cloned in a vector suitable for this purpose it was first modified. cDNA (5 µg) was dissolved in 100 µl of buffer containing 30 mM sodium acetate (pH 5.6), 50 mM NaCl, 1 mM $ZnSO_4$ and 21 U Mung Bean Nuclease. After incubation for 30 minutes at 37° C. the reaction was stopped by adding EDTA to 10 mM and Tris to 25 mM. After extraction with phenol/chloroform/isoamyl alcohol (25:24:1) the mixture was desalinated over a Sephadex G50 column.

The following were added to the eluate (125 µl): Tris pH 7.6 to 50 mM, EDTA to 2.5 mM, DTT to 5 mM, S'-adenosylmethionine to 0.5 µm and 100 U EcoRI-methylase. After incubation for 30 minutes at 37° C., the reaction was stopped by heating for 15 minutes at 65° C., after which 1/10 volume of a solution containing Tris-HCl 100 mM, $MgCl_2$ 100 mM and NaCl 500 inM (pH 7.5) was added, and, at the same time, each dNTP to 1 mM and 12.5 U Klenow DNA-polymerase. The reaction was stopped by adding an equal volume of phenol/chloroform/isoamyl alcohol (25:24:1) after incubating for 60 minutes at 22° C. The supernatant liquor was precipitated after adding 350 µl $H_2O$ and 50 µl 3 M sodium acetate (pH 5.6) with 500 µl isopropanol. After dissolving in 100 µl $H_2O$, the pellet was desalinated over Sephadex G50 and the eluate precipitated with ethanol.

After dissolving the pellet in 24 µl $H_2O$, ligation was carried out in 50 µl by adding 2 µg EcoRI linker, Tris-HCl (pH 8.0) to 30 mM, $MgCl_2$ to 10 mM, dithiothreitol to 10 mM, ATP to 1 mM, gelatin to 0.1 mg/ml and 10 U $T_4$DNA-ligase. The reaction was stopped after 16 hours' incubation at 4° C. by heating (for 15 minutes at 70 ° C.) after which cutting was carried out with restriction endonuclease EcoRI in 210 µl buffer containing 100 mM Tris-HCl (pH 7.6), 50 mM NaCl, 10 mM $MgCl_2$, 2.5 mM DTT and 500 U EcoRI. After 90 minutes' incubation at 37° C., the reaction was stopped by means of extraction with an equal volume of phenol/chloroform/isoamyl alcohol (25:24:1). The supernatant liquor was precipitated with 2.5 volume ethanol after adding sodium acetate (pH 5.6) to 300 mM cDNA and linkers were separated by means of a Biogel A15m column. The cDNA was precipitated with ethanol, after which the precipitate was dissolved in Tris-HCl 10 mM, EDTA 0.1 mM (pH 7.6). The cDNA molecules were then cloned in phage λgt11 (4).

Screening of the cDNA banks with antibodies directed against sporozoites showed a positive reaction in 1 per 1000 phage clones. These antibodies were previously purified over protein A Sepharose®, and then diluted four times with 1×Tris salt (Tris-HCl 10 mM, NaCl 150 mM, pH 8.0)+ 0.05% Tween 20+10% Foetal Calf Serum (FCS) and incubated for two hours at 37° C. with the filter.

The filter was then washed 4 times, for 10 minutes each time, with 50 ml 1×Tris salt+0.05% Tween 20. For the second antibody incubation a conjugate of goat-antimouse antibodies and alkaline phosphatase was used (diluted 1 per 7500 in 1×Tris salt+0.05% Tween 20+10% FCS) and incubated for 30 minutes at 37° C., after which the filter was washed as described after the 1st antibody incubation. The colour reaction was carried out in Tris-HCl 100 mM, NaCl 100 mM, $MgCl_2$ 10 mM, (pH 9.6), in which 0.33 mg/ml Nitroblue tetrazolium and 0.17 mg/ml 5-bromo-4-chloro-3-indolyl phosphate were dissolved. The filters were evaluated after 30 minutes incubation at room temperature.

An immunopositive clone was plaque-purified and this clone, designated *E. acervulina*1A clone (λgt11Ea1A) was further characterized (FIG. 1).

Phage DNA was isolated (ref. 2) and cut with the enzyme EcoRI.

The EcoRI fragments were subcloned in M13mp18 and pBR327. In addition, the complete cDNA fragment was subcloned in pUC18. Restriction maps were made of these subclones in pBR327 and the nucleotide sequence of the M13 clones was determined completely (FIG. 2).

For expression of the fusion protein, a lysogenic strain was made in *E. coli* Y1089$^-$ (ref. 4). The protein was purified over a Proto-Sorb LacZ column (Promega®) before it was used in a chicken protection experiment.

EXAMPLE 2

Protection against *E. acervulina* infection

The fusion protein produced by clone λgt11Ea1A in *Escherichia coli* Y1089$^-$ was purified in accordance with Example 1. For this purpose the product was brought together with avridine (ref. 7) in a suitable buffer, such that 1 ml suspension contained 1 mg avridine and 0.1 mg product. This material was injected intramuscularly into 4-week-old chickens (white Leghorns) in a dose of about 50 µg product per chicken. After two weeks this innoculation was repeated with an identical dose. Ten days later the chickens were infected with 50,000 sporulated *E. acervulina* oocysts which were administered orally (challenge). The numbers of oocysts in the faeces were counted daily. As controls, chickens were also injected with killed sporozoites and merozoites of *E. acervulina* and with β-galactosidase, all suspended in 500 µg avridine per dose. The results of this experiment are given in Table 1. Each group contained five chickens and the numbers of oocysts are listed per chicken and are the total of four days excretion (day 3 to day 6 post-infection inclusive).

TABLE 1

| Antigen | "Immunisation" dose per chicken per injection | Oocyst excretion per chicken after challenge | % inhibition with respect to control |
|---|---|---|---|
| Sporozoites | $1 \times 10^7$ | $82.8 \times 10^7$ | 47 |
| Merozoites | $1 \times 10^7$ | $20.9 \times 10^7$ | 87 |
| LacZ-Ea1A | 50 µg | $62.2 \times 10^7$ | 60 |
| β-galactosidase | 50 µg | $143.7 \times 10^7$ | 8 |
| Challenge control | — | $155.8 \times 10^7$ | — |

Challenge: contained 50,000 sporulated oocyst of *E. acervulina* in 1 ml 15% sucrose solution and was administered orally.

EXAMPLE 3

Antibodies

Antibodies evoked in chickens with the product obtained according to Example 1 were found to react, in dilutions of up to 1:1600, against components of the invasive stages, sporozoites and merozoites of types such as *E. tenella*, *E. acervulina* and *E. maxima*. These components are mainly localized in the foremost section of these stages where the penetration organelles, rhoptries and micronema are also located. In some chickens the antibodies were found to react around the Refractile Body of the sporozoites, especially of *E. tenella*.

EXAMPLE 4

Protection against *E. tenella* infection

The purified fusion protein was brought together with dioctadecylammonium bromide (DDA) in a suitable buffer, such that 1 ml of suspension contained 0.5 mg DDA and about 50 µg fusion protein. This material was injected intramuscularly into 3–4 week old chickens (white Leghorns) in a dose of about 50 µg fusion protein per chicken. After two weeks the chickens were orally challenged with 7500 sporulated *E. tenella* oocysts (Weybridge Strain). Seven days after the challenge injection the chickens were killed and lesions were scored on both ceca of each chicken. The lesions were scored according to the guidelines of Johnson and Reid (ref. 10). The results of this experiment are given in Table 2. From this, it is clear that a protein or a fragment thereof comprising at least a portion corresponding to the Ea1A polypeptide can be obtained from other Eimeria species. Each group contained five chickens.

TABLE 2

| Antigen | Immunisation dose | Lesion score ± SD |
|---|---|---|
| LacZ-Ea1A | 50 µg | 2.5 ± 1.2 |
| β-galactosidase | 50 µg | 3.5 ± 0.0 |
| challenge control | — | 3.3 ± 0.5 |

SD = standard deviation

EXAMPLE 5

Isolation and identification of Ea1A related DNA sequences from *E. tenella*

Construction of a cDNA library from *E. tenella*

For the construction of a cDNA library from *E. tenella* sporulated oocysts exactly the same procedure was followed as described in Example 1, except that the final cDNA preparation was cloned in phage λgt10 instead of phage λgt11 (4).

Screening of the *E. tenella* cDNA library with *E. acervulina* DNA

The 296 bp EcoRI fragment from pUC18/Ea1A was labeled with digoxigenin-dUTP by random priming, exactly following the protocol going with the "DNA labeling and detection kit, non-radioactive" from Boehringer, Mannheim (Cat. No. 1093657).

Filters containing immobilized DNA from the *E. tenella* cDNA library described above were prepared as described by Maniatis et al. (2) and probed by the freshly denatured (10 min. 95° C.), labeled *E. acervulina* fragment for 16 hours at 42° C. according to the manufacturer's instructions. Filters were washed as follows: twice for fifteen minutes with 2×SSC, 0.1% (w/v) SDS (1×SSC is 0.015 mol/l sodium citrate pH 7.0 plus 0.15 mol/l NaCl) at room temperature, twice for fifteen minutes with 1×SSC, 0.1% (w/v) SDS at 68∞ C., twice for thirty and once for fifteen minutes with 0.1×SSC, 0.1% (w/v) SDS at 68° C. and twice with PBS-tween (7.65 g/l NaCl, 0.91 g/l $Na_2HPO_4.2H_2O$, 0.21 g/l $KH_2PO_4$, 0.05% (v/v) Tween 80, pH 7.3) for 15 minutes at room temperature.

The filters were then reacted with a 1:5000 dilution in PBS-tween of polyclonal sheep anti-digoxigenin Fab-fragments, conjugated to alkaline phosphatase, for thirty minutes at room temperature. After washing the filters for four times fifteen minutes with PBS-tween at room temperature and once for fifteen minutes with 0.01M Tris-HCl pH 8.0, 0.15M NaCl, binding of the alkaline phosphatase to the filters was detected upon incubation with a solution of 0.33 g/l Nitroblue tetrazolium and 0.17 g/l 5-bromo-4-chloro-3-indolyl-phosphate in 0.1M Tris-HCl pH 9.6, 0.1M NaCl, 0.01M $MgCl_2$. One out of every 400 λgt10 *E. tenella* clones reacted with the *E. acervulina* probe; ten of these, called *E. tenella*1A1 to 10 (λgt10Et1A1 to 10) were plaque-purified. λgt10Et1A1 together with the Escherichia coli strain BNN102 have been deposited with the Centraal Bureau voor Schimmelcultures, Baarn (The Netherlands).

References

1) J. Pasternak et al.: Mol. & Bioch. Par. 3 (1981), 133–142.
2) T. Maniatis et al.: Molecular Cloning (Cold Spring Harbor Laboratory) 1982.
3) U. Gubbler et al.: Gene 25 (1983), 263–269.
4) T. V. Huynk et al.: DNA Cloning Techniques: A Practical Approach; D. Glover Oxford (1984).
5) J. P. Hopp et al.: Proc.Natl.Acad.Sci. U.S.A. 78 (1981), 3824–3828.
6) Ganish-Perron C.: Gene 33 (1985) 103–119.
7) K. E. Jensen in "Advances in carriers and adjuvants for Veterinary Biologics" ed. R. M. Nervig, P. M. Gough, M. L. Kaeberle, C. A. Whetstone. Iowa State Univ. Press. 1986, pp. 77–91.
8) P. Y. Chou et al.: Advances in Enzymology 47 (1987), 45–148.
9) M. F. Good et al.: Science 235 (1987), 1059–1062.
10) J. Johnson and W. M. Reid; Exp. Parasitology 28 (1970), 30–36.

What is claimed is:

1. An isolated polypeptide comprising the amino acid sequence of FIG. 2.

2. A vaccine for protecting poultry against coccidiosis caused by Eimeria parasites, comprising a polypeptide according to claim 1 and pharmaceutically acceptable excipients.

3. A vaccine for protecting poultry against coccidiosis caused by Eimeria parasites, comprising a microorganism which contains a recombinant DNA with a DNA fragment that encodes the polypeptide of claim 1.

4. A vaccine for protecting poultry against coccidiosis caused by Eimeria parasites, comprising a microorganism that contains a recombinant DNA, wherein said recombinant DNA encodes the polypeptide of claim 1.

* * * * *